US005750694A

United States Patent [19]
Jones et al.

[11] Patent Number: 5,750,694
[45] Date of Patent: May 12, 1998

[54] PROCESS FOR THE PREPARATION OF 4,6-DICHLOROPYRIMIDINE

[75] Inventors: John David Jones, Bury; Martin Charles Bowden, Rastrick; Stephen Martin Brown, Upper Cumberworth, all of United Kingdom

[73] Assignee: Zeneca Limited, London, England

[21] Appl. No.: 669,568

[22] PCT Filed: Mar. 27, 1995

[86] PCT No.: PCT/GB95/00676

§ 371 Date: Aug. 21, 1996

§ 102(e) Date: Aug. 21, 1996

[87] PCT Pub. No.: WO95/29166

PCT Pub. Date: Nov. 2, 1995

[30] Foreign Application Priority Data

Apr. 26, 1994 [GB] United Kingdom ............... 9408270

[51] Int. Cl.⁶ ........................................... C07D 239/30
[52] U.S. Cl. ........................................... 544/334
[58] Field of Search ........................................... 544/334

[56] References Cited

U.S. PATENT DOCUMENTS

| 4,659,827 | 4/1987 | Herd et al. | 544/299 |
| 5,352,787 | 10/1994 | Andres et al. | 544/309 |

FOREIGN PATENT DOCUMENTS

| 1082031 | 2/1994 | China . |
| 0 101 561 | 2/1984 | European Pat. Off. . |
| 0 183 092 | 6/1986 | European Pat. Off. . |
| 2 287 466 | 9/1995 | United Kingdom . |
| 91/01310 | 2/1991 | WIPO . |
| 94/07892 | 4/1994 | WIPO . |

OTHER PUBLICATIONS

Hull, R., "A New Synthesis of 4: 6–Dihydroxypyrimidines", J. Chem. Soc., (1951), p. 2214.
6–Diaminopyrimidine. A New Synthesis of Pyrimidine Derivatives, J. Chem. Soc., (1943), pp. 574–575.
Yanagida, Shozo, et al., "Studies on Nitrile Salts. II. A Facile One–step Synthesis of the Pyrimidine Nucleus", Bull. Chem. Soc. Japan, (1973), vol. 46, pp.299–301.
Chemical Abstracts, vol. 53, No. 219981, (1959).
Chemical Abstracts, vol. 113, No. 115234.
Chemical Abstracts, vol. 113, 115234, 1990.
Chemical Abstracts, vol. 113, 97564, 1990.
Chemical Abstracts, vol. 113, 78321, 1990.
Chemical Abstracts, vol. 113, 23838, 1990.
Chemical Abstracts, vol. 112, 55765, 1990.
Chemical Abstracts, vol. 111, 57357, 1989.
Chemical Abstracts, vol. 110, 172946, 1989.
Chemical Abstracts, vol. 110, 95143, 1989.
Chemical Abstracts, vol. 107, 23647, 1987.
Chemical Abstracts, vol. 107, 58962, 1987.
Chemical Abstracts, vol. 103, 215248, 1985.
Chemical Abstracts, vol. 104, 19434, 1986.
Chemical Abstracts, vol. 106, 196369, 1987.
Chemical Abstracts, vol. 105, 43176, 1986.
Chemical Abstracts, vol. 122, 81393, 1995.
Derwent Abstracts, No. 92–309033/38, 1992.
Derwent Abstracts, No. 02846X/02, 1976.

*Primary Examiner*—John M. Ford
*Attorney, Agent, or Firm*—Marian T. Thomson; Joseph R. Snyder

[57] ABSTRACT

A process for preparing 4,6-dichloropyrimidine comprising treating 4,6-dihydroxy-pyrimidine with phosgene in the presence of a suitable base and optionally in the presence of a solvent.

8 Claims, No Drawings

PROCESS FOR THE PREPARATION OF 4,6-DICHLOROPYRIMIDINE

This is a 35 U.S.C. §371 national stage application of PCT/GB 95/00676, filed 27 Mar. 1995.

The present invention relates to a process for converting 4,6-dihydroxypyrimidine (1) into 4,6-dichloropyrimidine (2) using phosgene and a suitable base. 4,6-Dichloropyrimidine is useful as a chemical intermediate in the agrochemical industry. It is especially useful in the preparation of ICIA5504.

It is known, for example, that phosphoryl chloride in the presence of dimethylaniline will convert 4,6-dihydroxypyrimidine to 4,6-dichloropyrimidine (Journal Chemical Society (1943) 574–5, and ibid (1951) 2214). The problem with these methods is that, when used on a large scale, a considerable amount of phosphoric acid by-product is produced and this must be disposed of in some way.

The present invention provides a process for preparing 4,6-dichloropyrimidine comprising treating 4,6-dihydroxypyrimidine with phosgene in the presence of a suitable base.

4,6-Dihydroxypyrimidine (1) can also exist in the tautomeric forms (A) and (B) and references to 4,6-dihydroxypyrimidine include all its tautomeric forms.

Suitable bases include tertiary amines of formula $R^1R^2R^3N$ (wherein $R^1$, $R^2$ and $R^3$ are, independently, $C_{1-10}$ alkyl, aryl, heteroaryl or aryl($C_{1-4}$)alkyl) and heterocyclic amines optionally substituted by $C_{1-10}$ alkyl. Examples of tertiary amines are triethylamine, 4-(N,N-dimethylamino)-pyridine, N,N-diisopropylethylamine and especially dimethylaniline. Examples of heterocyclic amines are pyridine, 2-methylpyridine, 4-methylpyridine, imidazole and N-alkyl pyrrolidines (such as N-methylpyrrolidine).

It is preferred that the base:phosgene molar ratio is in the range 1:10 to 10:1, especially in the range 1:1 to 1:4 (such as 2:3 and 2:4.5).

Alkyl groups are straight or branched chain and, unless stated otherwise, preferably contain from 1 to 6, especially from 1 to 4, carbon atoms. Examples are methyl, ethyl, iso-propyl, n-propyl, n-butyl and tert-butyl.

Aryl is preferably phenyl.

Heterocyclic amines are preferably saturated or unsaturated 3–7 membered carbon nitrogen rings. They are, for example, pyridine, imidazole, pyrrolidine or piperidine.

Heteroaryl is a 3–7 membered carbon nitrogen ring. It is, for example, pyridine, imidazole, pyrazole or pyrrolidine.

It is preferred that the process is carried out in a solvent or mixture of solvents. Chlorinated solvents (such as dichloromethane, 1,1,2,2-tetrachloroethane or chlorobenzene), ethers (such as tetrahydrofuran, glyme, diglyme or triglyme), polar aprotic solvents are preferred. Mixtures of solvents include, for example, a mixture of acetonitrile and dichloromethane.

The process is preferably carried out in the temperature range –10° C. to 130° C., especially 0°C. to 120° C., particularly 10° C. to 90° C.

In one aspect the present invention provides a process for preparing 4,6-dichloropyrimidine comprising adding phosgene to a mixture of 4,6-dihydroxypyrimidine and a suitable base.

In a further aspect the present invention provides a process for preparing 4,6-dichloropyrimidine comprising adding phosgene to a mixture of 4,6-dihydroxypyrimidine and a suitable base, wherein all the phosgene to be used in the process is added at the beginning of the process.

In another aspect the present invention provides a process for preparing 4,6-dichloropyrimidine comprising adding phosgene to a mixture of 4,6-dihydroxypyrimidine and a suitable base (such as dimethylaniline or diisopropylethylamine) in a chlorinated solvent, wherein the molar ratio of 4,6-dihydroxypyrimidine:suitable base:phosgene is in the range 1:(0.8 to 2.5):(2.5 to 3.6) especially in the range 1:(1.5 to 2.2):(2.9 to 3.3).

In yet another aspect the present invention provides a process for preparing 4,6-dichloropyrimidine comprising adding phosgene to a mixture of 4,6-dihydroxypyrimidine and a suitable base (such as dimethylaniline or diisopropylethylamine) in a nitrile solvent, wherein the molar ratio of 4,6-dihydroxypyrimidine:suitable base:phosgene is in the range 1:(0.1 to 2.4):(4 to 9) especially in the range 1:(0.1 to 2.1):(4.4 to 6.5).

In a further aspect the present invention provides a process for preparing 4,6-dichloropyrimidine the process comprising adding phosgene to a mixture of 4,6-dihydroxypyrimidine and a suitable base (such as dimethylaniline) in a suitable solvent (such as dichloromethane, acetonitrile or tetrahydrofuran), all the phosgene to be used in the process being added at the beginning of the process, and heating the reaction mixture (preferably for 1 to 30, especially 1 to 6 or 15 to 24 hours). The suitable base can be recovered (in salt form) during the product isolation and can be recycled.

The following Examples illustrate the invention. The apparatus used in the following Examples was dried before use, and reactions were conducted under nitrogen using anhydrous conditions.

EXAMPLE 1

4,6-Dihydroxypyrimidine (0.94 g) was suspended in dichloromethane, dimethylaniline (1.12 g) added and phosgene (5 g) was then condensed into the mixture. The resulting mixture was heated at reflux for 24 hours, then cooled and poured into water. High pressure liquid chromatographic (hplc) analysis of the resulting organic layer showed a 4,6-dihydroxypyrimidine: 4,6-dichloropyrimidine ratio of 39:58.

EXAMPLE 2

4,6-Dihydroxypyrimidine (20.5 g) was dispersed with agitation in dichloromethane (400 ml). Dimethylaniline (40.4 g) was added to the agitated mixture and the system was sealed (except for a vent line to a scrubber). Phosgene gas (56 g) was introduced from a cylinder and condensed onto a cold finger and collected in a pressure equalised dropping funnel. Once collected, the phosgene liquid was added to the reaction mixture over 15 minutes. The mixture was heated and agitated at reflux (29° C. approximately) for 17 hours after which time the mixture was cooled to room temperature and the excess phosgene removed by sparging with nitrogen.

Water (400 ml) was added slowly to the agitated reaction mass with cooling to maintain the temperature at ambient. The organic layer was separated, and the aqueous was then extracted with dichloromethane (2×100 ml). The combined extracts were dried over anhydrous sodium sulphate and concentrated by rotary evaporation to give 4,6-dichloropyrimidine as an orange crystalline solid (27 g), equivalent to a yield of 80% (hplc analysis).

EXAMPLE 3

4,6-Dihydroxypyrimiidine (2.0 g) was dispersed with agitation in acetonitrile (40 ml), dimethylaniline (2.1 g) was added and the mixture was heated to 50° C. Phosgene gas (14.6 g) was added to the mixture (by bubbling through the mixture) over 1 hour. The mixture was kept at 50° C. for 4.5 hours, cooled to room temperature, and the excess phosgene removed by sparging with nitrogen. Analysis (hplc) of the resulting reaction mass showed it to comprise 4,6-dichloropyrimidine (in 81% yield).

EXAMPLE 4

To a mixture of 4,6-dihydroxypyrimidine (5.14 g, 1 equivalent) and imidazole (6.19 g, 2 equivalents) in acetonitrile (100 ml) was added phosgene (28 g, 6.2 equivalents). The resulting mixture was stirred for 2¼ hours at room temperature and for 1 hour at 50° C. The reaction mixture was purged with nitrogen overnight and then partitioned between water and dichloromethane. The organic layer was separated and the aqueous extracted twice more with dichloromethane. The organic extracts were combined, washed with water (twice), dried over magnesium sulphate and evaporated to dryness to leave 4,6-dichloropyrimidine as a pale yellow solid.

EXAMPLE 5

To a stirred mixture of 4,6-dihydroxypyrimidine (5.18 g, 1 equivalent) and 4-(N,N,-dimethylamino)pyridine (0.55 g, 0.1 equivalent) in acetonitrile (100 ml) was added phosgene (28 g, 19.7 ml, 6.2 equivalents) in two aliquots. The resulting mixture was stirred for 10 minutes at room temperature and was then stirred for 4 hours at 55° C. The reaction mixture was purged with air after which water (200 ml) was added. The resulting mixture was extracted with dichloromethane (3×100 ml). The organic extracts were combined, washed with water (100 ml), dried over magnesium sulphate and evaporated to dryness to leave 4,6-dichloropyrimidine (4.63 g).

EXAMPLE 6

To a stirred mixture of 4,6-dihydroxypyrimidine (5.18 g, 1 equivalent) and N,N-diisopropylethylamine (11.75 g, 2 equivalents) in acetonitrile (100 ml) was added phosgene (28 g, 19.7 ml, 6.2 equivalents) in two aliquots. The resulting mixture was stirred for 10 minutes at room temperature and was then stirred for 4 hours at 55° C. The reaction mixture was sparged with air overnight after which water (100 ml) was added. The resulting mixture was extracted with dichloromethane (3×100 ml). The organic extracts were combined, washed with water (100 ml), dried over magnesium sulphate and evaporated to dryness to leave 4,6-dichloropyrimidine (6.35 g).

CHEMICAL FORMULAE (In Description)

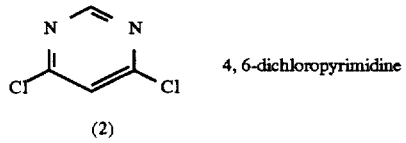

4, 6-dichloropyrimidine (2)

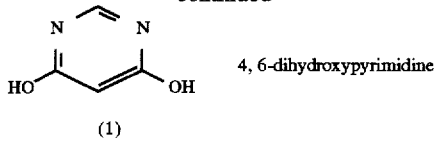

4, 6-dihydroxypyrimidine (1)

COCl$_2$ phosgene

POCl$_3$ phosphoryl chloride

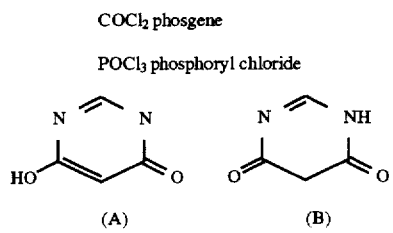

(A)          (B)

We claim:

1. A process for preparing 4,6-dichloropyrimidine comprising treating 4,6-dihydroxypyrimidine with phosgene in the presence of a base selected from the group consisting of: a tertiary amine of formula $R^1R^2R^3N$ wherein $R^1$, $R^2$ and $R^3$ are, independently, $C_{1-10}$ alkyl, phenyl, an aromatic 3–7 membered carbon nitrogen ring or phenyl($C_{1-4}$)alkyl: or a saturated or unsaturated 3–7 membered carbon nitrogen ring optionally substituted by $C_{1-10}$ alkyl.

2. A process as claimed in claim 1 wherein the base:phosgene molar ratio is in the range 1:10 to 10:1.

3. A process as claimed in claim 1 wherein the process is carried out in a solvent or mixture of solvents said solvent or solvents being selected from the group consisting of chlorinated solvents, ethers or polar aprotic solvents.

4. A process as claimed in claim 1 wherein the base is a tertiary amine of formula $R^1R^2R^3N$ (wherein $R^1$, $R^2$ and $R^3$ are, independently $C_{1-10}$ alkyl, phenyl, an aromatic 3–7 membered carbon nitrogen ring or phenyl($C_{1-4}$)alkyl): or a saturated or unsaturated 3–7 membered carbon nitrogen ring optionally substituted by $C_{1-10}$ alkyl.

5. A process as claimed in claim 1 wherein phosgene is added to a mixture of 4,6-dihydroxypyrimidine and base.

6. A process as claimed in claim 1 wherein the process comprises adding phosgene to a mixture of 4,6-dihydroxypyrimidine and base in a chlorinated solvent, wherein the molar ratio of 4,6-dihydroxypyrimidine:base:phosgene is in the range 1:(0.8 to 2.5):(2.5 to 3.6).

7. A process as claimed in claim 1 wherein the process comprises adding phosgene to a mixture of 4,6-dihydroxypyrimidine and base in a nitrile solvent, wherein the molar ratio of 4,6-dihydroxypyrimidine:base:phosgene is in the range 1:(0.1 to 2.4):(4 to 9).

8. A process as claim 1 wherein the base is dimethylanilane or diusopropylethylamine.

\* \* \* \* \*